United States Patent [19]
Oliver et al.

[11] Patent Number: 5,237,084
[45] Date of Patent: Aug. 17, 1993

[54] PREPARATION OF DIALKYL (N-CYANOIMIDO)CARBONATES FROM DIALKYL IMIDOCARBONATES AND CYANOGEN HALIDES

[75] Inventors: Michael A. Oliver; Ward H. Oliver, both of Baton Rouge, La.

[73] Assignee: Ciba-Geigy Corporation, Ardsley, N.Y.

[21] Appl. No.: 823,518

[22] Filed: Jan. 21, 1992

Related U.S. Application Data

[63] Continuation of Ser. No. 717,745, Jun. 19, 1991, abandoned.

[51] Int. Cl.$^5$ .............. C07C 271/68; C07C 261/00; C07C 269/00; C07C 269/06
[52] U.S. Cl. ............................................ 558/9; 558/6
[58] Field of Search ...................................... 558/6, 9

[56] References Cited

U.S. PATENT DOCUMENTS

| | | | |
|---|---|---|---|
| 2,708,189 | 5/1955 | Nelb et al. ........................ | 558/9 X |
| 2,819,292 | 1/1958 | Welcher et al. ..................... | 558/6 |
| 3,225,077 | 12/1965 | Schaefer et al. .................... | 558/9 |
| 4,298,544 | 11/1981 | Robinson ........................... | 558/9 X |

Primary Examiner—Floyd D. Higel
Attorney, Agent, or Firm—Kevin T. Mansfield; Edward McC. Roberts

[57] ABSTRACT

Dialkyl (N-cyanoimido) carbonates are prepared in good yield in a non-aqueous solvent by a process which comprises either (a) adding a cyanogen halide at a controlled rate to a reactor containing an unsubstituted or substituted dialkyl imidocarbonate, an inorganic base and/or a trialkyl amine, or (b) by adding a trialkyl amine to a solution of the unsubstituted or substituted dialkyl imidocarbonate and a cyanogen halide. The dialkyl imidocarbonate precursors are prepared by using a stoichiometric ratio (2:1) of alcohol to cyanogen halide in the presence of an acid acceptor and in a non-aqueous solvent.

Dialkyl (N-cyanoimido)carbonates are useful as intermediates for pesticides and pharmaceuticals.

18 Claims, No Drawings

PREPARATION OF DIALKYL (N-CYANOIMIDO)CARBONATES FROM DIALKYL IMIDOCARBONATES AND CYANOGEN HALIDES

This is a continuation of Ser. No. 717,745 filed Jun. 19, 1991, and now abandoned.

This invention relates to a process for the preparation of dialkyl (N-cyanoimido)carbonates. More particularly it relates to a process for the preparation of unsubstituted or substituted dialkyl (n-cyanoimido)carbonates which comprises reacting a cyanogen halide with a dialkyl imidocarbonate in the presence of a stoichiometric amount of a trialkyl amine or a catalytic amount of a trialkyl amine and an inorganic base. It also relates to the synthesis of an unsubstituted or substituted dialkyl imidocarbonate in a non-protic solvent using a stoichiometric ratio (2:1) of an alcohol to cyanogen halide.

Dialkyl (N-cyanoimido)carbonates are important products which find uses as intermediates for pesticides and pharmaceuticals. Other routes to said compounds are known and are discussed for example in U.S. Pat. Nos. 3,225,077 and 4,298,544 and German Offenlegungsschrift DE-OS-3225249. In general, the processes of the prior art are not satisfactory from the standpoints discussed below.

According to the prior art, a dialkyl imidocarbonate is reacted with cyanamide to give a dialkyl (N-cyanoimido)carbonate. The prior art is not satisfactory from the standpoint that it requires the use of cyanamide, an expensive and unstable reagent, and/or the process requires water or a two-phase system wherein one phase is water as the solvent. This necessitates an extraction to isolate the product.

It has now been found that dialkyl (N-cyanoimido) carbonates can be prepared in good yield in a non-aqueous solvent by a process which comprises either (a) adding a cyanogen halide at a controlled rate to a reactor containing an unsubstituted or substituted dialkyl imidocarbonate, an inorganic base and or a trialkyl amine, or (b) by adding a trialkyl amine to a solution of the unsubstituted or substituted dialkyl imidocarbonate and a cyanogen halide.

It has also been found that the dialkyl imidocarbonate precursor can be prepared by using a stoichiometric ratio (2:1) of alcohol to cyanogen halide in the presence of an acid acceptor and in a non-aqueous solvent. The prior art uses aqueous or mixed aqueous/water-immiscible solvent systems and a large excess of the alcohol. It has now been found that the reaction of the dialkyl imidocarbonate with cyanogen halides is best run under nearly anhydrous conditions. The use of a non-aqueous solvent system in the preparation of the dialkyl imidocarbonate eliminates the need to extract the product from an aqueous solution prior to the reaction with the second equivalent of the cyanogen halide. The prior art is also unsatisfactory because the excess alcohol must be removed from the system before reaction with the second equivalent of cyanogen halide to insure maximum yields of dialkyl (N-cyanoimido)carbonate.

In addition to the reactions discussed herein, the solution of dialkyl imidocarbonate can be also used without isolation to make other products such as 1,1-dialkoxy-2,2-dicyanoethylenes and, 1-alkoxy-1-amino-2,2-dicyanoethylenes (Chem. Ber., 1967, 100, 2064.)

Preferred dialkyl (N-cyanoimido)carbonates are of the formula I

wherein $R_1$ and $R_2$ are the same and are $C_1$-$C_6$alkyl which is unsubstituted or substituted by $C_1$-$C_3$alkoxy, phenyl or $C_3$-$C_6$cycloalkyl; or $R_1$ and $R_2$ may be part of an alkyl chain to form an optionally substituted 5 or 6 membered ring. This ring may be fused to a benzo ring system.

The alkyl groups $R_1$ and $R_2$ may be straight chain or branched, $R_1$ and $R_2$ are for example methyl, ethyl, n-propyl, isopropyl, n-butyl, sec-butyl, isobutyl and tert-butyl plus the isomeric pentyl and hexyl groups. Methyl and ethyl are preferred.

$C_3$-$C_6$cycloalkyl includes cyclopropyl, cyclobutyl, cyclopentyl and cyclohexyl with cyclopropyl preferred.

$C_1$-$C_3$alkoxy includes methoxy, ethoxy, propoxy and isopropoxy.

Ring systems formed by $R_1$ and $R_2$ can be for example, 1,3-dioxolane, 1,3-dioxane, or 1,3-benzodioxolane. Suitable substituents for the 1,3-dioxane or 1,3 dioxolane rings include methyl, ethyl, propyl or isopropyl. Suitable substituents for the aromatic ring of the 1,3-benzodioxolane include $C_1$-$C_4$alkyl, $C_1$-$C_4$alkoxy or halo. 1,3-Dioxolane is preferred.

Preferred dialkyl imidocarbonates are of the formula II

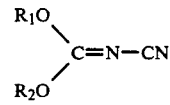

wherein $R_1$ and $R_2$ are as defined for formula I.

Preferred cyanogen halides are cyanogen chloride or cyanogen bromide. Cyanogen chloride is most preferred.

Alcohols useful in the preparation of dialkyl (N-cyano)imidocarbonates include straight or branched chain $C_1$-$C_6$alcohols such as for example methyl, ethyl, n-propyl, isopropyl, n-butyl, sec-butyl, isobutyl and tert-butyl plus the isomeric pentyl and hexyl alcohols. Methyl and ethyl alcohol are preferred. These $C_1$-$C_6$alcohols may be unsubstituted or substituted by $C_1$-$C_3$alkoxy, phenyl or $C_3$-$C_6$cycloalkyl. 1,2- and 1,3-Diols such as ethylene glycol, 1,2- and 1,3-propylene glycol, 1,2-, 1,3- and 2,3-butylene glycol and 1-phenyl-1,2-ethanediol which will form an optionally substituted 5 or 6 membered ring are also suitable alcohols. This ring may be part of a fused benzo ring system if pyrocatechol or an alkylated derivative thereof is employed as the diol.

The bases used in the preparation of dialkyl (N-cyano)imidocarbonates include trialkylamines and alkali metal carbonates with a trialkylamine catalyst. Preferred radicals for the trialkylamines include straight or branched chains of 1 to 8 carbons wherein one or more of the carbon atoms may be replaced by an oxygen atom. The alkyl substituents of the amine may be part of ring systems, for example N-methylmorpholine and N-methylpiperidine. Preferred trialkylamines are trimethylamine and triethylamine. Preferred alkali metal carbonates are sodium carbonate and potassium carbonate. Suitable amounts of trialkylamine catalyst are 1 to 10 mole %, with 2 to 4 mole % being preferred.

If an alkali metal carbonate is used as the base in the reaction of a cyanogen halide with a dialkyl imidocarbonate, a small amount of water is necessary to activate the alkali metal carbonate. However, large amounts of water are detrimental to yields. Preferred amounts of water are 0.5 to 5 moles of water per mole of alkali metal carbonate charged, with 0.5 to 2 moles of water being particularly preferred.

Suitable solvents for the reaction of the dialkyl imidocarbonate with a cyanogen halide include open chain and cyclic ethers, halocarbons, aromatic hydrocarbons, halogenated aliphatic and aromatic hydrocarbons, ketones and esters. Ethers are the most preferred solvents. Other preferred solvents include $C_1$-$C_3$ketones, $C_1$-$C_6$-hydrocarbons substituted by 1-6 halogens, and benzene and phenyls substituted by 1-2 halogens or $C_1$-$C_3$alkyl groups. Preferred individual solvents include for example, diethyl ether, tert-buty methyl ether, tetrahydrofuran, dioxane, methylene chloride, toluene and acetone.

Temperatures for the reaction of a cyanogen halide with the dialkyl imidocarbonate can range from $-20°$ to $40°$ C., preferably from about $-10°$ to $10°$ C.

For the reaction of a cyanogen halide with a dialkyl imidocarbonate, modes of addition include adding the cyanogen halide to a solution of the dialkyl imidocarbonate, adding the base to a solution of the dialkyl imidocarbonate and cyanogen halide, or concurrent addition of the dialkyl imidocarbonate and base to a solution of cyanogen halide. Adding the cyanogen halide to a solution of the dialkyl imidocarbonate and base is preferred.

Suitable acid acceptors for the preparation of the dialkyl imidocarbonates are alkali metal hydroxides or alkali metal alkoxides having the same alkyl moiety as in the desired dialkyl imidocarbonate. If the dialkyl imidocarbonate solution is to be isolated and an alkali metal hydroxide is used as the acid acceptor, two equivalents of the hydroxide should be used. The second equivalent will adsorb the water generated in the reaction and the resulting salt/hydroxide slurry can then be removed by filtration. The solution of dialkyl imidocarbonate thus obtained can be used in subsequent reactions. Preferred alkali metal hydroxides are sodium hydroxide or potassium hydroxide. Preferred alkali metal alkoxides include sodium methoxide and sodium ethoxide.

Suitable solvents for the reaction to form the dialkyl imidocarbonate are ethers, halocarbons, halogenated hydrocarbons and aromatic hydrocarbons, for example, diethyl ether, tert-butyl methyl ether, tetrahydrofuran, dioxane, methylene chloride or toluene. Ethers are the preferred solvents, with tert-butyl methyl ether particularly preferred.

Temperatures for the reaction to form the dialkyl imidocarbonate can range from $-20°$ to $20°$ C., preferably from about $-10°$ to $5°$ C.

The two reactions can be run in sequence in a single reactor if one equivalent of alkali metal hydroxide or alkali metal alkoxide, and one to two equivalents of an alkali metal carbonate are used as the bases. The carbonate an be added at the beginning of the first cyanogen halide addition or prior to the second cyanogen halide addition. The trialkylamine catalyst should not be added before the formation of the dialkyl imidocarbonate is complete. A minimum hold time of two hours at 0° C. is required before the addition of the catalyst and the second equivalent of the cyanogen halide.

The preferred method for carrying out the reactions in sequence is to slurry one equivalent of sodium hydroxide and one and a half equivalents of sodium carbonate in an ether solvent. Two equivalents of an alcohol are added while cooling the mixture to about 0° C. Cyanogen chloride is then added over about a four hour period while maintaining a reaction temperature of 0°-5° C. The reaction mixture is held at 0°-5° C. for two hours while the reaction to form the dialkyl imidocarbonate is completed. After the hold period is complete, 2-4 mole % of a trialkylamine and a molar equivalent of water are added. The second equivalent of cyanogen chloride is then added over a 2-4 hour period while maintaining a temperature of 0°-5° c. After an optional hold period, the reaction is filtered to remove the salts and the solvent evaporated to yield the crude dialkyl (N-cyanoimido)carbonate.

The invention is illustrated but not limited by the following examples. Cyanogen chloride solutions in tert-butyl methyl ether (MTBE) used for most examples were prepared in the laboratory and typically contained 1-2% water. Therefore unless otherwise specified, no additional water was added to the reaction mixture when cyanogen chloride from this source was used.

EXAMPLE 1

Dimethyl (N-cyanoimido)carbonate

To a 500 ml reactor is added 150 ml of tert-butyl methyl ether (MTBE) and 25.3 g (0.633 mole) of sodium hyroxide in bead form. The reactor contents are cooled to 0° C. and 20.5 g of methanol (0.639 mole) is charged while maintaining the reaction temperature at 0° to 5° C. Then 19.4 g of gaseous cyanogen chloride is charged over 1.5 hours while maintaining the temperature at $-5°$ to 0° C. The reaction mixture is held at 0° C. for an additional two hours. At the end of the hold period, 37.0 g of sodium carbonate, 1.5 g of trimethylamine (25% in water, 7 mmol), and 3.5 g water is added to the reaction mixture. 20.5 g of cyanogen chloride is charged over 1.5 hours while maintaining the temperature at 31 5° to 0° C. The reaction mixture is held at 0° C. for one hour then warmed to 25° C. The reaction mixture is filtered and the solvent is evaporated from the filtrate under vacuum. The salt cake is washed twice with 50 ml of methylene chloride and the filtrate is added to the crude product. The methylene chloride is evaporated under vacuum to obtain 23.1 g of dimethyl (N-cyanoimido)-carbonate. Assay 95.2%, (61% yield).

EXAMPLE 2

Dimethyl (N-cyanoimido)carbonate

To a 500 ml reactor is added 50 ml of tert-butyl methyl ether (MTBE) and 44.0 g (1.0 mole) of sodium hydroxide in bead form. The reactor contents are cooled to 0° C. and 32.0 g of methanol (1.00 mole) is charged while maintaining the reaction at 0° to 5° C. 100 g of a cyanogen chloride solution (31.0% in MTBE, 0.50 mole) is added to the stirred reaction mixture over 30 minutes while maintaining the temperature at 0° to 5°. After the addition is complete, the reaction mixture is held at $-5°$ to 0° C. overnight. The reaction mixture is filtered and then the salt cake is washed with 50 ml MTBE. The combined filtrates are added to a clean 1 liter flask along with 58.5 g of sodium carbonate, 3.6 g of trimethylamine (25% in water, 10 mmol), and 5.4 g water. The reactor contents are cooled to $-5°$ C. and 106 g (31% in MTBE, 0.53 mole) of cyanogen chloride solution is charged over 5 hours while maintaining the reaction mixture at 0° to 5° C. After the addition is complete, the reaction mixture is held for two hours at 0° to 5° C. The reaction mixture is then filtered and the cake is washed with 75 ml of MTBE. The filtrates are combined and the solvent is removed under vacuum to yield 28.3 dimethyl (N-cyanoimido)carbonate, 90% assay (45% yield).

EXAMPLE 3

Dimethyl (N-cyanoimido)carbonate

To a 500 ml reactor is added 50 ml of tert-butyl methyl ether (MTBE) and 40.0 g (1.0 mole) of sodium hydroxide in bead form. The reactor contents are cooled to 0° C. and 32.1 g of methanol (1.00 mole) is added while maintaining the reaction at 0° to 5° C. Then 104 g of a cyanogen chloride solution (29.4% in MTBE, 0.50 mole) is added to the stirred reaction mixture over 1.5 hours while maintaining the temperature at 0° to 5° C. After the addition is complete, the mixture is stirred at 0° C. for an additional 2 hours. At the end of the holding period the reaction mixture is filtered and the salts are washed with 50 ml of MTBE. The filtrates are combined, added to a clean flask and cooled to 0° to 5° C. Then 102.1 g of a cyanogen chloride solution (29.4% in MTBE, 0.49 mole) is added over 15 minutes. Maintaining the temperature at 0° to 5° C., 30 g of triethylamine (97%, water 2%) is added over 2.5 hours. When the addition is complete, the reaction mixture is filtered. Then the salt cake is washed three times with 75 ml of boiling MTBE. The solvent is removed under vacuum. Then the crystals are washed twice with 15 ml of ice cold MTBE. The product is dried under vacuum to obtain 23.2 grams of dimethyl (N-cyanoimido)carbonate, assay 93.9% (38% yield).

EXAMPLE 4

Diethyl (N-cyanoimido)carbonate

To a 1 liter rector is added 50 ml of tert-butyl methyl ether, 40 g (1.0 mole) of sodium hydroxide (beads) and 48.5 g of 95% ethanol (1.0 mole). The reactor contents are cooled to −5° C. and 103 g of cyanogen chloride solution (30% in MTBE, 0.50 mole) is added over 2 hours while stirring, maintaining the reaction mixture at −5° to 0° C. After the addition is complete, the mixture is stirred at 0° to 10° C. for an additional two hours. At the end of the period, the reaction mixture is filtered and the salt cake is washed with 50 ml MTBE. The combined filtrates are added to a clean 1 liter flask along with 58.3 g of sodium carbonate and 2.36 g of trimethylamine (25% in water, 10 mmol). The reactor contents are cooled to −5° C. and 103 g of cyanogen chloride solution (30% in MTBE, 0.50 mole) is added over 1 hour while maintaining the reaction mixture at 0° to 5° C. After the addition is complete, the mixture is stirred for one hour at 0° to 5° C., then warmed to 25° C. and held for an additional hour. The reaction mixture is filtered and the solvent is removed under vacuum to obtain 51.2 g diethyl (N-cyanoimido)carbonate, 82.5% assay (59.5% yield).

EXAMPLE 5

Di-n-propyl (N-cyanoimido)carbonate

To a 1 liter reactor is added 50 ml of tert-butyl methyl ether, 40 g (1.0 mole) of sodium hydroxide (beads) and 60.1 g of n-propanol (1.0 mole). The reactor contents are cooled to 0° C. and 96 g of cyanogen chloride solution is added (32.6% in MTBE, 0.50 mole) over 1.5 hours while maintaining the reaction temperature 0° to 5° C. After the addition is complete, the reaction mixture is stirred at 0° to 5° C. for an additional two hours. At the end of the hold period, the reaction mixture is filtered and the saltcake is washed with 50 ml MTBE. The combined filtrates are added to a clean 1 liter flask along with 58.3 g of sodium carbonate and 2.3 g of trimethylamine (25% in water, 10 mmol). The reactor contents are cooled to −5° C. and 96 g of a cyanogen chloride solution is added (32.6% in MTBE, 0.50 mole) over 1.5 hours while maintaining the reaction mixture at −5° to 5° C. After the addition is complete, the reaction mixture is stirred for one hour while allowing the temperature to slowly reach 20° C. The reaction mixture is then filtered and the solids are washed with 75 ml MTBE. The filtrates are combined and the solvent is removed under vacuum to yield 68.5 g di-n-propyl (N-cyanoimido)carbonate, 80.0% assay. (64.5% yield).

EXAMPLE 6

Diisopropyl (N-cyanoimido)carbonate

To a 1 liter reactor is added 50 ml of tert-butyl methyl ether, 40 g (1.0 mole) of sodium hydroxide (beads) and 60.1 g of isopropanol (1.0 mole). The reactor contents are cooled to 0° C. and 106 g of cyanogen chloride solution (29% in MTE, 0.50 mole) is charged over 2.5 hours while maintaining the reaction at −5° to 5° C. After the addition is complete, the reaction mixture is stirred at −5° to 5° C. for an additional two hours. At the end of the holding period the reaction mixture is filtered and the saltcake is washed with 75 and MTBE. The combined filtrates are added to a clean 1 liter flask along with 58.3 g of sodium carbonate and 2.36 g of trimethylamine (25% in water, 10 mmol). The reactor contents are cooled to −5° C. and 106 g of cyanogen chloride solution (29% in MTBE, 0.50 mole) is charged over 1.5 hours while maintaining the reaction mixture at −5° to 5° C. After the addition is complete, the reaction mixture is allowed to warm to 25° C. The reaction mixture is filtered and the solvent is removed under vacuum to yield 50.6 g diisopropyl (N-cyanoimido)carbonate, 90% assay. (53.6% yield).

What is claimed is:

1. A process for the preparation of an unsubstituted or substituted dialkyl (N-cyanoimido)carbonate which comprises reacting a cyanogen halide with an unsubstituted or substituted dialkyl imidocarbonate in the presence of a trialkyl amine or a catalytic amount of a trialkyl amine and an inorganic base.

2. A process according to claim 1, wherein the dialkyl (N-cyanoimido)carbonate is of the formula I

wherein
  R$_1$ and R$_2$ are the same and are C$_1$–C$_6$alkyl which is unsubstituted or substituted by C$_1$–C$_3$alkoxy, phenyl or C$_3$–C$_6$cycloalkyl; or
  R$_1$ and R$_2$ may be part of an alkyl chain which forms an unsubstituted or methyl, ethyl, propyl or isopropyl substituted 5-6 membered ring, which ring may be fused to a benzo ring system.

3. A process according to claim 2, wherein $R_1$ and $R_2$ are the same and are methyl, ethyl, propyl or isopropyl.

4. A process according to claim 1, wherein the cyanogen halide is cyanogen chloride or cyanogen bromide.

5. A process according to claim 1, wherein the inorganic base is an alkali metal carbonate.

6. A process according to claim 1, wherein the trialkyl amine is a tri($C_1$-$C_8$)alkylamine.

7. A process according to claim 6, wherein the trialkyl amine is trimethylamine or triethylamine.

8. A process according to clam 5 wherein 1 to 10 mole % of a trialkyl amine is used in addition to an alkali metal carbonate.

9. A process according to claim 8, wherein 2–4 mole % of triethyl- or trimethylamine is used, and the alkali metal carbonate is sodium carbonate or potassium carbonate.

10. A process according to claim 1, which is conducted in a non-aqueous solvent.

11. A process according to claim 10, wherein said solvent is an open chain or cyclic ether, a $C_3$-$C_7$ketone, a $C_1$-$C_6$hydrocarbon substituted with 1–6 halogens, benzene or a phenyl substituted with 1 or 2 halogens or $C_1$-$C_3$alkyl groups, or a mixture thereof.

12. A process according to claim 11, wherein the solvent is t-butyl methyl ether, tetrahydrofuran, acetone, or methylene chloride.

13. A process according to claim 1, wherein the temperature is in the range of $-20°$ to $40°$ C.

14. A process according to claim 13, wherein the temperature is in the range of $-10°$ to $10°$ C.

15. A process according to claim 1, which comprises adding a cyanogen halide to a solution of the dialkyl imidocarbonate and base, adding the base to a solution of the dialkyl imidocarbonate and cyanogen halide, or concurrent addition of the dialkyl imidocarbonate and base to a solution of cyanogen halide.

16. A process according to claim 15, which comprises adding the cyanogen chloride to a solution of the dialkyl imidocarbonate and base.

17. A process according to claim 1, which comprises of slurrying one equivalent of sodium hydroxide and one and a half equivalents of sodium carbonate in t-butyl methyl ether, adding two equivalents of an alcohol, cooling the mixture to about $0°$ C., adding one equivalent of cyanogen chloride over about a four hour period while maintaining a reaction temperature in the range of $0°$–$5°$ C., holding the reaction mixture in the same temperature range until the reaction to form the dialkyl imidocarbonate is essentially complete, adding 2–4 mole % of trimethylamine, 1 molar equivalent of water, adding a second equivalent of cyanogen chloride over a 2–4 hour period while maintaining a temperature of $0°$–$5°$ C., stirring until the reaction is essentially complete, filtering the mixture to remove salts and then evaporating the solvent to yield a crude dialkyl (N-cyanoimido)carbonate.

18. A process according to claim 17, wherein the alcohol is methanol, ethanol, n-propanol or isopropanol.

* * * * *